United States Patent
Ukil et al.

(10) Patent No.: US 10,548,533 B2
(45) Date of Patent: Feb. 4, 2020

(54) METHOD AND SYSTEM FOR REMOVING CORRUPTION IN PHOTOPLETHYSMOGRAM SIGNALS FOR MONITORING CARDIAC HEALTH OF PATIENTS

(71) Applicant: TATA CONSULTANCY SERVICES LIMITED, Mumbai (IN)

(72) Inventors: Arijit Ukil, Kolkata (IN); Soma Bandyopadhyay, Kolkata (IN); Chetanya Puri, Kolkata (IN); Arpan Pal, Kolkata (IN); Kayapanda Mandana, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 426 days.

(21) Appl. No.: 15/456,112

(22) Filed: Mar. 10, 2017

(65) Prior Publication Data

US 2017/0273632 A1 Sep. 28, 2017

(30) Foreign Application Priority Data

Mar. 14, 2016 (IN) .............................. 201621008875

(51) Int. Cl.
*A61B 5/00* (2006.01)
*G16H 50/20* (2018.01)
(Continued)

(52) U.S. Cl.
CPC ........ *A61B 5/7207* (2013.01); *A61B 5/02416* (2013.01); *A61B 5/6815* (2013.01);
(Continued)

(58) Field of Classification Search
CPC ... A61B 5/02416; A61B 5/6826; A61B 5/725; A61B 5/7207; A61B 2576/00
See application file for complete search history.

(56) References Cited

U.S. PATENT DOCUMENTS 8,755,854 B2  6/2014 Addison et al.
9,918,666 B2 *  3/2018 Yousefi ................. A61B 5/024
(Continued)

FOREIGN PATENT DOCUMENTS

EP  2319397  5/2011

OTHER PUBLICATIONS

Guttag et al. "Real time reconstruction of quasiperiodic multi-parameter physiological signals", 2012 Eurasip Journal on Advances in Signal processing, pp. 1-15. (Year: 2012).*

(Continued)

*Primary Examiner* — Mohamed Charioui
(74) *Attorney, Agent, or Firm* — Finnegan, Henderson, Farabow, Garrett & Dunner LLP

(57) ABSTRACT

A method and system for removing corruption in photoplethysmogram (PPG) signals for monitoring cardiac health of patients is provided. The method is performed by extracting photoplethysmogram signals from the patient, detecting and eliminating corruption caused by larger and transient disturbances in the extracted photoplethysmogram signals, segmenting photoplethysmogram signals post detection and elimination of corruption caused by larger and transient disturbances, identifying of inconsistent segments from the segmented photoplethysmogram signals, detecting anomalies from the identified inconsistent segments of the photoplethysmogram signals, analysing the detected anomalies of the photoplethysmogram signals and identifying photoplethysmogram signal segments corrupted by smaller and prolonged disturbances.

16 Claims, 5 Drawing Sheets

(51) Int. Cl.
  *G16H 50/30* (2018.01)
  *A61B 5/024* (2006.01)
(52) U.S. Cl.
  CPC .......... *A61B 5/6826* (2013.01); *A61B 5/6829* (2013.01); *A61B 5/6898* (2013.01); *A61B 5/725* (2013.01); *A61B 5/7264* (2013.01); *A61B 5/7278* (2013.01); *G16H 50/20* (2018.01); *G16H 50/30* (2018.01); *A61B 5/0004* (2013.01); *A61B 5/7246* (2013.01); *A61B 2576/00* (2013.01)

(56) References Cited

U.S. PATENT DOCUMENTS

| | | | |
|---|---|---|---|
| 9,974,487 B2* | 5/2018 | Lin | A61B 5/02438 |
| 2010/0079279 A1 | 4/2010 | Watson et al. | |
| 2010/0090798 A1 | 4/2010 | Garcia Molina et al. | |
| 2016/0038045 A1* | 2/2016 | Shapiro | A61B 5/02416 600/479 |
| 2017/0143272 A1* | 5/2017 | Brouse | A61B 5/7203 |
| 2018/0085011 A1* | 3/2018 | Ma | A61B 5/7203 |

OTHER PUBLICATIONS

Deshmane, A. V., "False Arrhythmia Alarm Suppression Using ECG, ABP, and Photoplethysmogram", Massachusetts Institute of Technology, pp. 1-93, (2009).

Li, Q. et al., "Dynamic time warping and machine learning for signal quality assessment of pulsatile signals", 2012 Institute of Physics and Engineering in Medicine Physiological Measurement, Institute of Physics and Engineering in Medicine, vol. 33, No. 9, Aug. 17, 2012.

Orphanidou, C. et al., "Signal-Quality Indices for the Electrocardiogram and Photoplethysmogram: Derivation and Applications to Wireless Monitoring", IEEE Journal of Biomedical and Health Informatics, IEEE, vol. 19, Issue: 3, pp. 832-838, May 2015.

Ganeshapillai, G. et al., "Real time reconstruction of quasiperiodic multiparameter physiological signals", EURASIP Journal on Advances in Signal Processing, Springer, Dec. 2012.

* cited by examiner

METHOD AND SYSTEM FOR REMOVING CORRUPTION IN PHOTOPLETHYSMOGRAM SIGNALS FOR MONITORING CARDIAC HEALTH OF PATIENTS

PRIORITY CLAIM

This U.S. patent application claims priority under 35 U.S.C. § 119 to: India Application No. 201621008875, filed on 14 Mar. 2016. The entire contents of the aforementioned application are incorporated herein by reference.

TECHNICAL FIELD

The present application generally relates to biomedical signal processing. Particularly, the application provides a method and system for removing corruption in photoplethysmogram (PPG) signals captured using a mobile communication device. More particularly, the application provides a method and system for removing corruption in photoplethysmogram (PPG) signals for monitoring cardiac health of patients.

BACKGROUND

An intriguing problem in healthcare analytics, particularly in photoplethysmogram (PPG) signals based proactive cardiac health monitoring, is the frequent presence of corruption in PPG signal from multiple noise sources like motion artifacts, ambient noise. Data preprocessing through denoising results in improved interpretation of the cardiovascular systems and removal of false alarms. In fact, the occurrence of high false alarms (precisely false positives due to the presence of noise) leads to 'alarm fatigue'. In contrary, high false negatives would be fatal to the patients.

In all practicality, it is infeasible to capture ECG or ABP signals without using extra sensors or through invasive procedures. It is observed that majority of computational techniques do not find widespread clinical use because of their lack of capability in reducing the artifacts and other noises. Prior art illustrates 80 different artifact detection techniques and it is perceived that most of the techniques are highly explicit, hard coded to suit for certain device settings, usage and thus limiting their applicability in almost all practical purposes. Current trend is towards multi-signal corruption analysis and detection. The underlying assumption is that all of the cardiological signals like viz. PPG, ECG, ABP cannot be corrupted simultaneously while source of corruption is independent. Stand-alone method of PPG signal denoising and quality assessment is presented in prior art, which employs computationally heavy machine learning algorithms and multivariate 'voting' threshold mechanism. Such schemes are not suitable for smartphones to deliver real-time performance. Another problem is the single-stage error detection is itself erroneous and prone to have high false negatives.

Thereby, removing corruption in photoplethysmogram (PPG) signals for monitoring cardiac health of patient's negatives is still considered to be one of the biggest challenges of the technical domain.

SUMMARY

Embodiments of the present disclosure present technological improvements as solutions to one or more of the above-mentioned technical problems recognized by the inventors in conventional systems. For example, in one embodiment, a method for removing corruption in photoplethysmogram (PPG) signals for monitoring cardiac health of patients is provided. The method comprises extracting photoplethysmogram signals from the patient, detecting and eliminating corruption caused by larger and transient disturbances in the extracted photoplethysmogram (PPG) signals, segmenting photoplethysmogram (PPG) signals post detection and elimination of corruption caused by larger and transient disturbances, identifying of inconsistent segments from the segmented photoplethysmogram (PPG) signals, detecting anomalies from the identified inconsistent segments of the photoplethysmogram (PPG) signals, analysing the detected anomalies of the photoplethysmogram (PPG) signals and identifying photoplethysmogram (PPG) signal segments corrupted by smaller and prolonged disturbances.

In another embodiment, a system for removing corruption in photoplethysmogram (PPG) signals for monitoring cardiac health of patients is provided. The system (200) comprises of an image capturing device (202) coupled with a mobile communication device (204), an extrema elimination module (206), a segmentation module (208), an inconsistency identification module (210), an anomaly detection module (212), an anomaly analytics module (214) and a decision module (216).

In yet another embodiment, a non-transitory computer readable medium storing instructions is disclosed wherein when executed by a possessor on a system, the instructions cause the processor to perform method for monitoring cardiac health of patients comprising extracting photoplethysmogram signals from the patient, detecting and eliminating corruption caused by larger and transient disturbances in the extracted photoplethysmogram (PPG) signals, segmenting photoplethysmogram (PPG) signals post detection and elimination of corruption caused by larger and transient disturbances, identifying of inconsistent segments from the segmented photoplethysmogram (PPG) signals, detecting anomalies from the identified inconsistent segments of the photoplethysmogram (PPG) signals, analysing the detected anomalies of the photoplethysmogram (PPG) signals and identifying photoplethysmogram (PPG) signal segments corrupted by smaller and prolonged disturbances.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
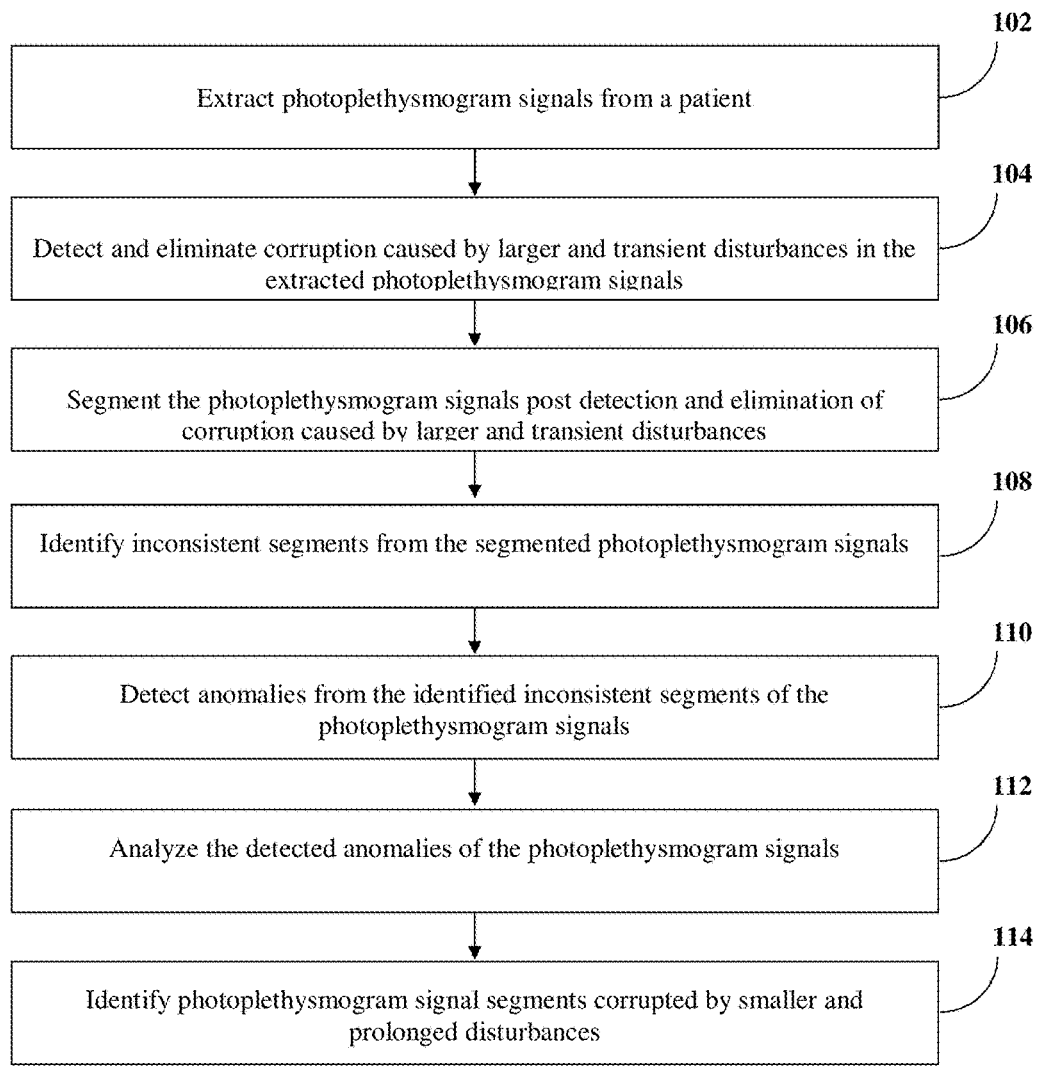
FIG. 1 shows a flowchart illustrating method for removing corruption in photoplethysmogram (PPG) signals for monitoring cardiac health of patients.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The present disclosure provides a method and system for removing corruption in photoplethysmogram (PPG) signals for monitoring cardiac health of patients.

In an embodiment of the present invention, a system (200) for removing corruption in photoplethysmogram (PPG) signals for monitoring cardiac health of patients comprises of an image capturing device (202) coupled with a mobile communication device (204), an extrema elimination module (206), a segmentation module (208), an inconsistency identification module (210), an anomaly detection module (212), an anomaly analytics module (214) and a decision module (216).

Referring to FIG. 1, it is a flow chart illustrating a method for removing corruption in photoplethysmogram (PPG) signals for monitoring cardiac health of patients.

The process starts at step 102, photoplethysmogram signals are extracted from the user using the image capturing device (202) coupled with the mobile communication device (204). At the step 104, corruption caused by larger and transient disturbances in the extracted photoplethysmogram signals are detected and eliminated. At the step 106, photoplethysmogram (PPG) signals post detection and elimination of corruption caused by larger and transient disturbances are segmented. At step 108, inconsistent segments from the segmented photoplethysmogram signals are identified. At step 110, anomalies from the identified inconsistent segments of the photoplethysmogram signals are detected. At step 112, the detected anomalies of the photoplethysmogram signals are analyzed and at step 114, photoplethysmogram (PPG) signal segments corrupted by smaller and prolonged disturbances are identified.

Figure 2:
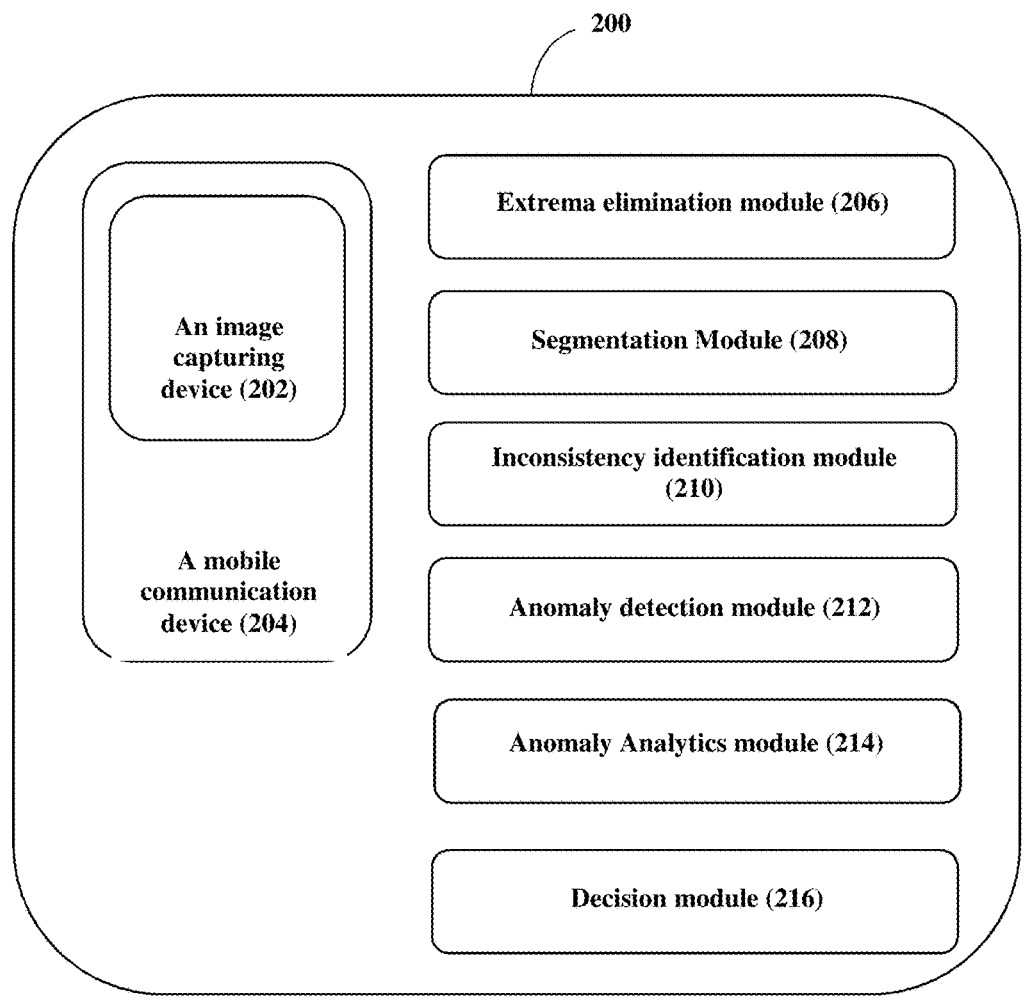
FIG. 2 shows a block diagram of a system for removing corruption in photoplethysmogram (PPG) signals for monitoring cardiac health of patients.

Referring to FIG. 2, it is a block diagram illustrating system architecture for removing corruption in photoplethysmogram (PPG) signals for monitoring cardiac health of patients.

In another embodiment of the present invention, the image capturing device (202) coupled with the mobile communication device (204) is adapted for extracting photoplethysmogram signals from the patient. The photoplethysmogram signals are extracted from patient's peripheral body parts selected from a group comprising but not limited to finger, ear, and toe. In a specific embodiment, the photoplethysmogram signals are extracted from user's forehead. The mobile communication device (204) captures photoplethysmogram signal in reflective mode. The mobile communication device (204) is selected from a group comprising of smart phone, mobile phone, laptop, tablet, and personal digital assistant.

The image capturing device (202) coupled with the mobile communication device (204) is a camera and have a light emitting source for extracting photoplethysmogram signals from the patient's peripheral body parts selected from a group comprising but not limited to finger, ear, toe; forehead, thereby, obtaining a video sequence of the light, reflected from patient's peripheral body parts.

Figure 3A:
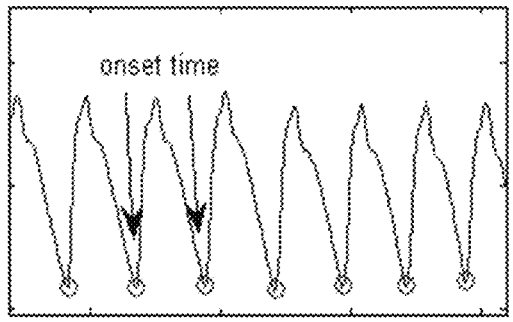
FIG. 3A shows a shows a clean or expected photoplethysmogram (PPG) signal.
Figure 3B:
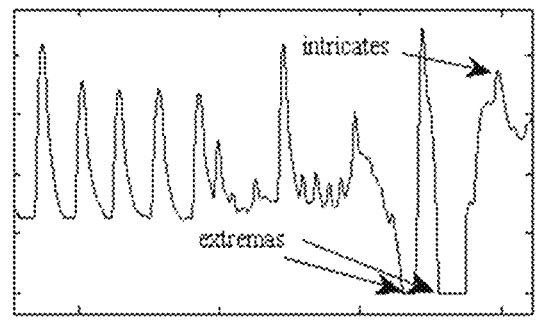
FIG. 3B shows a corrupted photoplethysmogram (PPG) signal with extrema corruption and intricate corruption.

Corruption in PPG signal induces erroneous feature extraction and eventually leads to wrong diagnosis. The corruption in PPG is classified as: 1. Extremas and 2. Intricates, where extremas are the corruptions due to larger, transient disturbance and intricates are due to smaller and mostly prolonged disturbances as shown in FIG. 3. Three classes of PPG signal corruption are also defined to model the corruption process as: Error or corruption dominant, normal sample dominates, random mix of both.

In another embodiment of the present invention, the extremas are first processed for—to detect the larger variation of corruption, which would help in unbiased analysis.

In another embodiment of the present invention, let $P=\{p_n\}$, $n=1, 2, \ldots, N$ be the captured PPG signal. Firstly, PPG is filtered to remove the residual invalide sections because human Heart Rate (HR) is a bounded variable and PPG cannot have frequency components beyond that bound. PPG signal $P=\{p_n\}$ is passed through a low pass filter (LPF) with transfer function:

$$H(z) = \frac{(1-z^{-5})^2}{(1-z^{-2})^2}.$$

In another embodiment of the present invention, a modified Thompson Tau technique is considered to statistically decide the inconsistencies on the filtered PPG signal for finding the extremas— a. Find median absolute deviation $\theta_n = |p_n - \text{median}(P)|$, $\forall n \in N$.

b. Find the threshold of discard $$\tau = \frac{t_{\frac{\alpha}{2},(n-1)}}{n^{\frac{1}{2}} \cdot \left(n - 2 + t_{\frac{\alpha}{2}}^2\right)^{\frac{1}{2}}},$$

where $$t_{\frac{\alpha}{2}}$$

is the critical student t's value with $\alpha=0.05$ with single degree of freedom.

c.

$$\begin{cases} \theta_n > \tau \to \text{outlier} \\ \theta_n \leq \tau - \text{normal} \end{cases}, \varepsilon x = \{\theta_n > \tau\}$$

are the extremas, $\varepsilon x \in P$.

d. Discard $\varepsilon x$ from the set, and continue from (a) with $P=\{P-\varepsilon x\}$ until $\{\varepsilon x\}=\emptyset$.

e. P with all extremas εx removed is stored for further processing.

Figure 4:
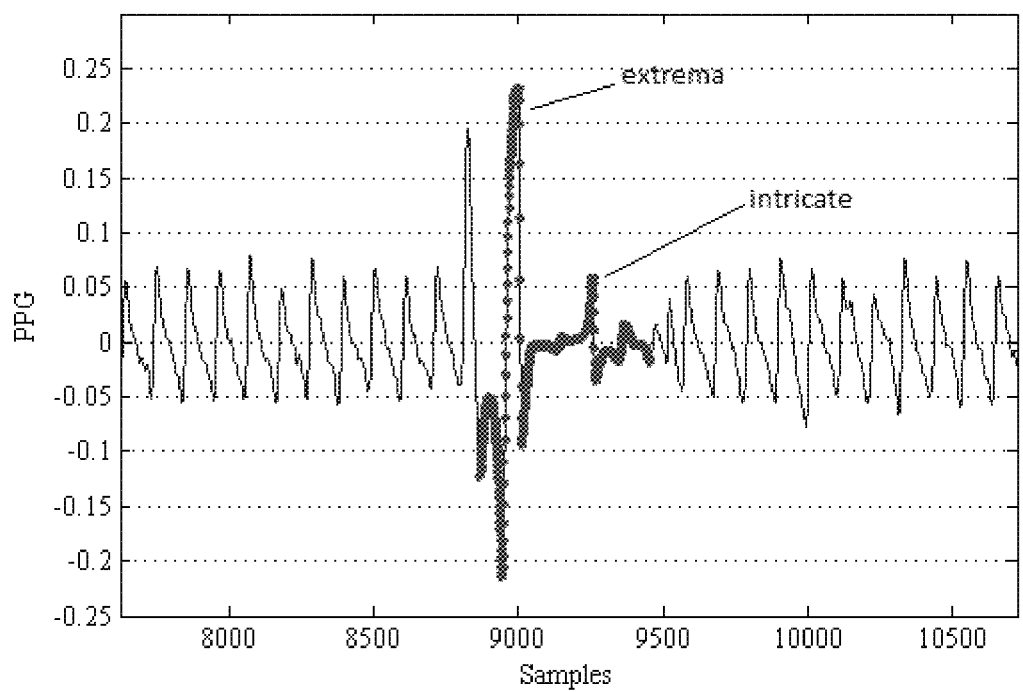
FIG. 4 is shows extrema corruption and intricate corruption in photoplethysmogram (PPG) signal.

In an exemplary embodiment of the present invention, the extremas detection of PPG signal of patient # v748s is depicted (data taken from publicly available MIT-Physionet challenge 2015) in FIG. 4.

In another embodiment of the present invention, the below table depicts the notational meanings of the symbols used—

| Notation | Meaning |
| --- | --- |
| $P = \{p_n\}$, | PPG signal |
| $o_k$ | Cardiac cycle time instants derived from PPG signal |
| $\Omega_k = \{o_{k-1}:o_k\}$ | Onset time duration |
| $l_p$ | Most probable onset time duration |
| $\psi_k$ | Peak-to-peak duration at the cardiac cycle |
| $\mathbb{T}$ | Template of a normal PPG segment of unit cardiac cycle |

With successful extremas detection, decorrupting the entire PPG becomes less error prone. In the next steps, intricate detection takes place.

PPG signal is a time series records sampled at a predefined frequency. It consists of series of continuous segments and each segment start is indicated by cardiac cycle onset time (FIG. 5) and each segment identifies a single complete heart beat and onset duration $\Omega(\Omega_k=\{o_{k-1}:o_k\}$, $k=1, 2, \ldots K)=\{\Omega_k\}$. is detected. From $\Omega$, the most probable onset duration with the assumption that for a short period (around 1 minute) is derived. The intricate corruptions are distinguished through dissimilar measurement by applying a normalized dynamic window-adaptive Dynamic Time Warping (NDWADTW) method.

In another embodiment of the present invention, most probable onset duration is computed using a method to estimate individual's cardiac characteristics. In the said method, two parameters $\bar{\omega}$,n are to be tuned, where $\bar{\omega}$,n are the distance and density parameters respectively, where $\bar{\omega}$ is defined as the furthest distance for which a point is density-reachable and n is the minimum number of points required to form a density cluster. The underlying philosophy is: Let $\mathcal{D}$ be the distance of an arbitrary point ρ in $\Omega$ to its at least n−1 nearest neighbors, so the $\mathcal{D}$ -neighborhood (spherical) contains at least n points. The most probable value of (even if $\Omega \neq \mathcal{N}(\mu,\sigma))$ $\bar{\omega}(=\mathcal{D})$ for least false positive) is $\bar{\Omega}=[3\sigma]$. Let $\Omega^1 \ldots, \Omega^M$ be the M clusters following $\bar{\omega}, \eta$. Anomalous segment lengths $\Omega'$ are the subset in $\Omega$ that are not part of any $\Omega^m$, m=1, 2, . . . . M and $\Omega^N$ (normal segment length)=$\Omega-\Omega'$ and $l_p$ (most probable segment length)=median($\Omega^N$)=$\overline{\Omega^N}$.

In another embodiment of the present invention, PPG being a deterministic signal (at least the valid PPG signal would always maintain certain pattern) and each segment length carries that signature or pattern. The most obvious PPG cardiac segment sample is considered as the template $\mathbb{T} :=\{t_1, \ldots, t_M\}$ of length M corresponds to most common human heart rate of 72 beats per minute.

To counter the nonlinearity in the PPG segments, each segment is restricted to most probable segment length $l_p$, i.e. $\Omega_k=\{\omega_1, \omega_2, \ldots, \omega_{l_p}\}_k$ consists of $l_p$ sample points. However, restricting segment length would underestimate the probability of significantly diverge segment length for cardio-abnormal patients. So, the following adaptive segment length computation method is proposed and implemented— a. Find segment length of each PPG segment $l_k=|\omega_k|$, $k \forall K$.
b. Compute length-invalidity threshold $\mathcal{I}=HR|_{max} \times \mathcal{F} \times 60$, where $\mathcal{F}$=sampling frequency and $HR|_{max}$=280 beats per minute (bpm) (safe assumption of highest human heart rate).
c. Compute adaptive length-abnormality threshold $\mathcal{A}_k=\text{const} \times (\omega_p \cdot l_p + \Sigma_{i=1}^3 \omega_i \cdot \Omega_{k \mp i})$ and $\Sigma_{i=1}^N \omega_i + \omega_p = 1$. We consider const=1.2, $$N = 3; \omega_p = 0.5, \omega_i = \frac{0.5}{2N}.$$

d. Length abnormal PPG segments are $$\Omega_k |_{length-abnormal} = \begin{cases} |\Omega_k| \geq \mathcal{I}_{th} \\ |\Omega_k| \geq \mathcal{A}_k \end{cases}.$$

e. $l_p=|\Omega_k|$, $\forall \Omega_k \in \Omega_k|_{length-abnormal}$, i.e. for the length abnormal PPG segments, most probable segment length $l_p$ is its own segment length.

In order to compute the dissimilarity of given PPG segment, distance is measured with the computed 'Morphologically Valid PPG Template' (MVPT). Let $P^\lambda:=\{p_1, p_2, \ldots, p_L\}$ be the PPG signal of length $L \in \mathbb{N}$ for segment $\lambda$ and $\mathbb{T}:=\{t_1, t_2, \ldots, t_M\}$ be the template MVPT of length $M \in \mathbb{N}$. In order to accommodate the non-stationary nature and nonlinearity in each of the segments due to dynamicity of cardiac output, heart beat rate for single person and person to person, normalized dynamic window-adaptive dynamic time warping (NDWADTW) is introduced here. Instead of computing on the entire length of each PPG segment at cardiac cycle $\{o_{k-1}-o_k\}$ (which is variable in length due to change of heart rate), the temporal-length mismatch bias is eliminated by fixing the analysis segment length of a person to its most probable segment length, i.e. $L=l_p$.

With two stages of decorruption performed through extremas and segment length variability detection, finally normalized dynamic window-adaptive dynamic time warping (NDWADTW) distance is computed to address the amplitude-abnormality and is applied for PPG signal cleaning. Each segment is normalized as $$\Omega_k \rightarrow \Omega_k \times \frac{\max(\mathbb{T})}{\max(\Omega_k)}$$

that minimizes the effect of nonlinear changes in the amplitude of each segment due to changes in cardiac output. Thus the similarity measurement is individual-adaptive and is not biased with the non-stationary nature and nonlinearity of the segment lengths. Normalized dynamic window-adaptive dynamic time warping (NDWADTW) distance $\delta_{\Omega_k \mathbb{T}}$ is computed between template $\mathbb{T}$ and each of the segments $$\Omega_k=\{\omega_1, \omega_2, \ldots, \omega_{l_p}\}_k,$$

$k \forall K$ of the extracted PPG signal of lengths M, $l_p$ respectively as:

$$\delta_{\Omega_k,T} = \delta([\omega_1, \omega_2, \ldots, \omega_{l_p}], [t_1, t_2, \ldots, t_M]) =$$

$$\mathcal{D}(\omega_{l_p}, t_M) + \min \begin{cases} ([\omega_1, \omega_2, \ldots, \omega_{l_{p-1}}], [t_1, t_2, \ldots, t_{M-1}]) \\ ([\omega_1, \omega_2, \ldots, \omega_{l_p}], [t_1, t_2, \ldots, t_{M-1}]) \\ ([\omega_1, \omega_2, \ldots, \omega_{l_{p-1}}], [t_1, t_2, \ldots, t_M]) \end{cases}$$

Where $$\mathcal{D}(\omega, t) = Eucl(\omega, t) := \sqrt{\Sigma_{i=1}^{N}(\omega_i - t_i)^2}$$

Figures 5A, 5B:
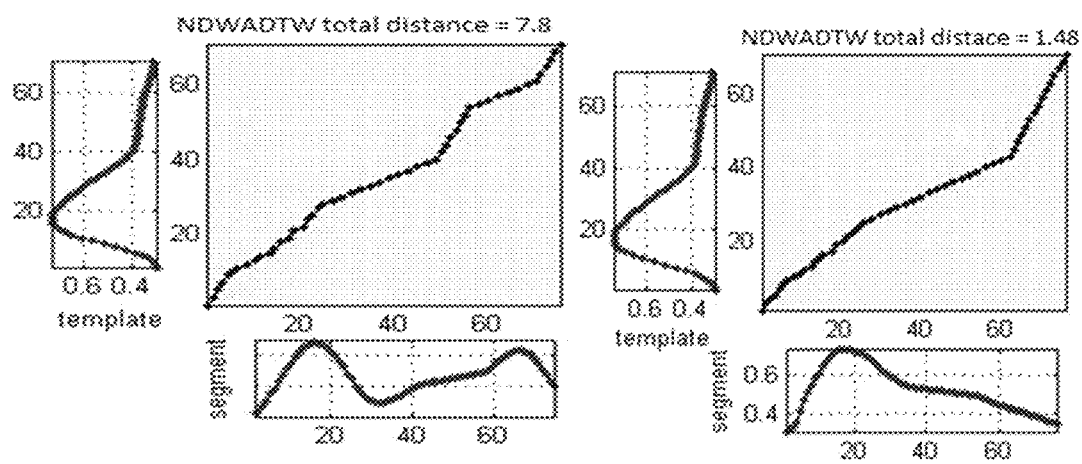
FIG. 5A shows normalized dynamic window-adaptive dynamic time warping distance of corrupted photoplethysmogram (PPG) signal segment.
FIG. 5B shows normalized dynamic window-adaptive dynamic time warping distance of clean photoplethysmogram (PPG) signal segment.

In FIG. 5, it is noticed that $\delta_{\Omega_k,T}$ is higher for seemingly corrupt segments.

To classify the PPG segments as corrupt or non-corrupt, robust extreme value analysis is performed, which requires masking effect and swamping effect are to be minimized. Masking effect causes one or more anomalous or corrupt points to get undetected, while normal or non-corrupt points are depicted as outlier by swamping effect. As it is intuitive as well as evident from FIG. 4 that higher NDWADTW distance is associated with corrupt points, the objective is to minimize the masking effect.

For minimizing masking effect, masking breakdown point $\xi_M$ is to be close to 0.5. For a large class of identifier Hampel identifier, a nonlinear local outlier detector based on Median Absolute Deviation (MAD) scale estimation provides outlier detection with $\xi_M \rightarrow 0.5$ as follows:

MAD($\varepsilon_N$)=median(|$\varepsilon_1$–median($\varepsilon_N$)|, . . . ,|$\varepsilon_N$–median ($\varepsilon_N$)|)

An observation is identified as corrupt when: Typically Thr=3 is considered. The Hampel identifier is applied to decide whether a DTW distance is corrupt. When Hampel identifier declares a NDWADTW distance outlier, the corresponding PPG segment is declared as corrupt.

In an exemplary embodiment of the present invention, Total 750 patients from four hospitals in the USA and Europe are chosen at random and publicly available as MIT-BIH arrhythmia Physionet CinC Challenge 2015 datasets. Corrupt-segments are manually annotated through crowd-sourcing. Random 25 PPG signals out of 750 are taken and number of annotators annotates the corrupt regions and voting result is used as ground truth. Exemplary case of de-corruption of PPG signal for patient # v748s is shown in FIG. 4.

In another embodiment of the present invention, the dynamic multi-level cluster-based anomaly analytics implemented herein is described below:
a. Segments with normalized dynamic window-adaptive dynamic time warping (NDWADTW) distance greater than a threshold (thresh) are corrupt, where thresh=median (ceil(dtw$_{ppg}$))+scale*(mad(ceil(dtw$_{ppg}$), 1)), scale=1.5.
b. To find segments that still remain undetected, a multiple stage clustering approach, 2-means followed by 3-means is taken.
c. K-means is applied on the derived DTW distances of all segments from the template.
d. K-Means with k=2 segregates these points into two clusters with centers c1, c2 (c2>c1). This is done to verify if there are any segments in cluster c2 that are outliers. This is done by checking the distance between these two centroids.
e. If |c1−c2|>n*s, where s=std(dtw_ppg), then K-means with k=3 is applied on the DTW distances to find out elements in c1',c2',c3'. Elements in c2',c3' are considered outliers that remained undetected in the step above.
f. Burst sequences of corrupt sequences is checked, if there are at most 'num' number of segments present between two detected corrupt segments, then all segments in between are rendered corrupt.

In another embodiment of the present invention, multi-level cluster-based anomaly analytics implemented herein is dynamic in nature because of the system's ability to adapt to the changing nature of the PPG signals.

In another embodiment of the present invention, as prediction problem is evaluated by confusion matrix parameters: False Positives (FP), False Negatives (FN), True Positives (TP) and True Negatives (TN) are shown in the table below. It is observed that have achieved very low false negatives (<=4%), indicating that the very less number of non-detections. With such mechanism of PPG signal de-corruption, better heart condition status and lesser false alarms are expected.

|  | Predicted (Yes) | Predicted (No) |
| --- | --- | --- |
| Actual (Yes) | TP = 24% | FN = 4% |
| Actual (No) | FP = 14% | TN = 58% |

In an exemplary embodiment of the present invention, 20 subjects with 10 lab-generated and 10 from MIMIC 2 datasets from physionet have been considered—the performance in terms of precision=78%, recall=80% and specificity=96%.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for removing corruption in photoplethysmogram (PPG) signals for monitoring cardiac health of patients; said method comprising:
    extracting photoplethysmogram (PPG) signals using an image capturing device coupled with a mobile communication device;
    detecting and eliminating corruption caused by transient disturbances in the extracted photoplethysmogram (PPG) signals;
    segmenting the photoplethysmogram (PPG) signals post detection and elimination of corruption caused by transient disturbances;
    identifying inconsistent segments from the segmented photoplethysmogram (PPG) signals;
    detecting anomalies from the identified inconsistent segments of the photoplethysmogram (PPG) signals;
    analyzing the detected anomalies of the photoplethysmogram (PPG) signals; and
    identifying photoplethysmogram (PPG) signal segments corrupted by prolonged disturbances.

2. The method according to claim 1, wherein the photoplethysmogram signals are extracted from the patients' peripheral body parts.

3. The method according to claim 1, wherein the patients' peripheral body parts are selected from a group comprising fingertip, ear, toe and forehead.

4. The method according to claim 1, wherein the photoplethysmogram signals are extracted from the user using a light emitting source attached to the image capturing device coupled with the mobile communication device.

5. The method according to claim 1, wherein the image capturing device coupled with the mobile communication device extracts photoplethysmogram signals as a video stream.

6. The method according to claim 1, wherein the detection and elimination of corruption caused by transient disturbances in the extracted photoplethysmogram (PPG) signals is performed by using a Thompson Tau technique.

7. The method according to claim 1, wherein identification of inconsistent segments from the segmented photoplethysmogram (PPG) signals is performed using normalized dynamic window-adaptive dynamic time warping (NDWADTW) method.

8. The method according to claim 7, wherein the normalized dynamic window-adaptive dynamic time warping (NDWADTW) method is implemented with respect to a dynamic and patient specific PPG signal template.

9. The method according to claim 8, wherein the patient specific PPG signal template is a personalized and morphologically valid photoplethysmogram (PPG) template.

10. The method according to claim 1, wherein detection of anomalies from the identified inconsistent segments of the photoplethysmogram (PPG) signals is performed using a hampel filter.

11. The method according to claim 1, wherein analysis of the detected anomalies of the photoplethysmogram (PPG) signals is performed using a dynamic multi-level cluster-based anomaly analytics method.

12. The method according to claim 1, wherein identification of photoplethysmogram (PPG) signal segments corrupted by prolonged disturbances is based on the analysis of the detected anomalies arising out of one or more sources, wherein the anomalies arising out of one or more sources are selected from a group comprising external noise, internal noise, motion artifacts and physiological condition.

13. The method according to claim 12, wherein identification of photoplethysmogram (PPG) signal segments corrupted by prolonged disturbances is performed to identify anomalies arising out of external noise, internal noise and motion artifacts.

14. The method according to claim 1, wherein identification of photoplethysmogram (PPG) signal segments corrupted by prolonged disturbances is performed by providing a binary decision with respect to the analyzed photoplethysmogram (PPG) signal segments.

15. A system for removing corruption in photoplethysmogram (PPG) signals for monitoring cardiac health of patients; said system comprising:
    an image capturing device coupled with a mobile communication device adapted for extracting photoplethysmogram signals from the user; and
    a processor configured for:
        detecting and eliminating corruption caused by transient disturbances in the extracted photoplethysmogram (PPG) signals;
        segmenting the photoplethysmogram (PPG) signals post detection and elimination of corruption caused by transient disturbances;
        identifying inconsistent segments from the segmented photoplethysmogram (PPG) signals;
        detecting anomalies from the identified inconsistent segments of the photoplethysmogram (PPG) signals;
        analyzing the detected anomalies of the photoplethysmogram (PPG) signals; and
        identifying photoplethysmogram (PPG) signal segments corrupted by prolonged disturbances.

16. A non-transitory computer readable medium storing instructions which when executed by a possessor on a system, cause the processor to perform a method for monitoring cardiac health of patients comprising:
    detecting and eliminating corruption caused by transient disturbances in the extracted photoplethysmogram (PPG) signals;
    segmenting the photoplethysmogram (PPG) signals post detection and elimination of corruption caused by transient disturbances;
    identifying inconsistent segments from the segmented photoplethysmogram (PPG) signals;
    detecting anomalies from the identified inconsistent segments of the photoplethysmogram (PPG) signals;
    analyzing the detected anomalies of the photoplethysmogram (PPG) signals; and
    identifying photoplethysmogram (PPG) signal segments corrupted by prolonged disturbances.

* * * * *